United States Patent [19]

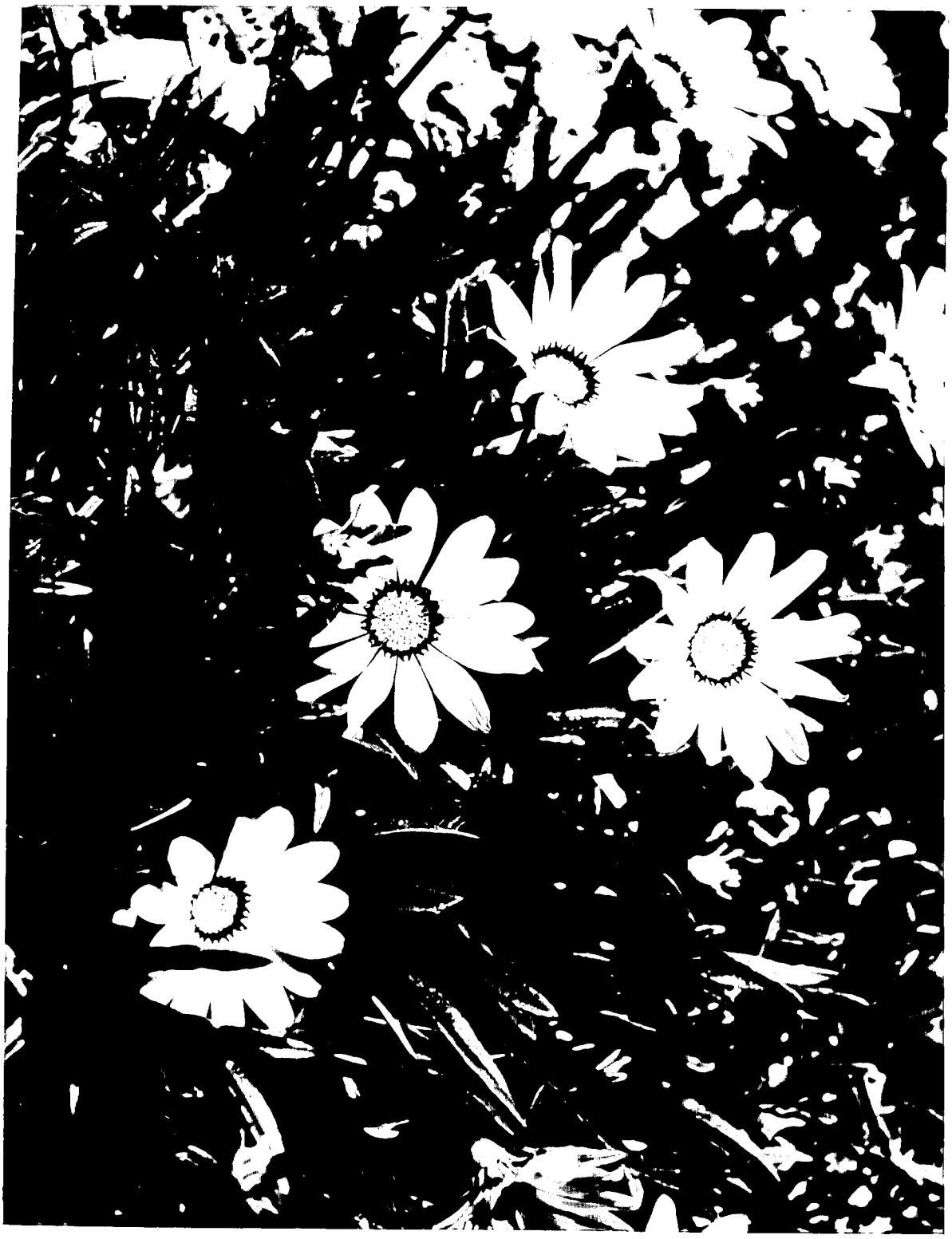

Ono

[11] Patent Number: Plant 5,795

[45] Date of Patent: Nov. 4, 1986

[54] GAZANIA PLANT CALLED MITSUWA SUPER CLUMP

[75] Inventor: Toshiaki Ono, Chatsworth, Calif.

[73] Assignee: Mitsuwa Nursery, Inc., Moorpark, Calif.

[21] Appl. No.: 746,524

[22] Filed: Jun. 19, 1985

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Roylance, Abrams, Berdo & Goodman

[57] ABSTRACT

A Gazania named Mitsuwa Super Clump having yellow flowers, and characterized by, as compared to known clumping yellow Gazanias, of being much more hardy and vigorous, with longer leaves, taller flowers, and growing more rapidly.

1 Drawing Figure

BACKGROUND OF THE INVENTION

The present invention relates to a new and distinctive cultivar of gazania plant, botanically known as *Gazania splendens*, and referred to commercially by the cultivar name "Mitsuwa Super Clump".

BRIEF DESCRIPTION OF THE INVENTION

Gazanias, in general, are a genus of herbs of the aster family which are characterized by large, showy, orange and yellow blossoms and which prefer bright sunshine. They are native to South Africa but are now widely cultivated and are commercially important. Gazanias were named after Theodorus Gaza, a medieval Greek scholar of Italy.

DESCRIPTION OF THE DRAWING

The accompanying color photograph, forming a part of this disclosure, was taken in March of 1985 in Moorpark, Calif., and shows Mitsuwa Super Clump growing in a bed; the view being a perspective looking down and forwardly at the plant. The photograph shows the colors of all parts of Mitsuwa Super Clump as true as is reasonably possible in this type of color photograph.

DETAILED DESCRIPTION

Mitsuwa Super Clump is a spontaneous sport or mutant discovered by Mr. Toshiaki Ono in the nursery of Mitsuwa Nursery, Inc. of Moorpark, Calif. The parent plant is *Gazania splendens aurantiacum.*

Asexual reproduction, starting by propagating cuttings from the originally discovered sport, has reproduced the unique features of this new plant through successive propagations. Crown cuttings (a major stem with several leaves) were used for this propagation. Mitsuwa Super Clump is distinguished from its parent and from all other commercial Gazanias in general by several characteristics.

Existing clumping gazanias have a severe disadvantage. Reference here is made to, botanically, *Gazania splendens aurantiacum,* commonly known as "South African Daisy". This plant has a bush-like growth habit, with green leaves that are very narrow. The problem with this prior known plant, in Southern California at least, is that it is so prone to disease that it has become unacceptable to landscapes, and thus lost to the commercial market.

Mitsuwa Super Clump has a much greater resistance to the many plant fungi and diseases which have decimated *Gazania splendens aurantiacum,* and has proved commercially acceptable as to its vigor and hardiness.

Mitsuwa Super Clump in addition has a significantly longer life span as compared to *Gazania splendens aurantiacum.*

The Mitsuwa Super Clump flowers are comparable in color and shape to those of *Gazania splendens aurantiacum.* However, the flowers different in several respects. Mitsuwa Super Clump flowers are each about 10% smaller than those of *Gazania splendens aurantiacum,* but the Mitsuwa Super Clump plant produces much more profusely, on the order of 30% more blossoms per plant. In addition Mitsuwa Super Clump blooms two to three weeks earlier than *Gazania splendens aurantiacum.* Both Mitsuwa Super Clump and *Gazania splendens aurantiacum,* in common with most Gazanias in Southern California, blooms more or less all year long.

The foliage of Mitsuwa Super Clump, compared to that of *Gazania splendens aurantiacum,* has narrower leaves, flowers which stand taller on their spikes, and produces a plant which is taller overall.

Mitsuwa Super Clump is much easier to propagate than the other commercial clumping Gazania, *Gazania splendens aurantiacum.* More specifically, the time needed to produce a root system for Mitsuwa Super Clump is about 30% less than the time needed to produce a root system for *Gazania splendens aurantiacum.* Further, in addition to producing root systems faster, the percentage of plants resulting from these root systems is significantly higher for Mitsuwa Super Clump than for *Gazania splendens aurantiacum.*

Color references herein, except where the ordinary dictionary meaning is clear from the context, are to The Royal Horticultural Color Chart. The following characterizations were made by the discoverer and other personnel of Mitsuwa Nursery, Inc., based on the flowers shown in the photograph herein.

Flower, petal upside, Yellow 9A
Flower, petal downside, Yellow 12C
Flower, marks in center, Black 202A
Flower, pale stripe on bottom of petals, Grey Brown 199
Leaves, upside, Green 137A
Leaves, downside, White 155D The buds display the characteristic roughly acorn shape common to other Gazanias.

I claim:

1. A new and distinct cultivar of Gazania named Mitsuwa Super Clump, as described and illustrated, and particularly characterized by its vigor and resistance to disease and fungi; and by its flowers on tall spikes and overall tall growth habit.

* * * * *